United States Patent
McKinnis et al.

(10) Patent No.: US 10,595,823 B2
(45) Date of Patent: Mar. 24, 2020

(54) INTERNAL ULTRASOUND ASSEMBLY FLUID SEAL

(71) Applicant: Muffin Incorporated, West Lafayette, IN (US)

(72) Inventors: Peter S. McKinnis, West Lafayette, IN (US); Yun Zhou, West Lafayette, IN (US); Sarah Robbins, Lafayette, IN (US); Neal E. Fearnot, West Lafayette, IN (US)

(73) Assignee: Muffin Incorporated, West lafayette, IN (US)

( * ) Notice: Subject to any disclaimer, the term of this patent is extended or adjusted under 35 U.S.C. 154(b) by 410 days.

(21) Appl. No.: 14/211,885

(22) Filed: Mar. 14, 2014

(65) Prior Publication Data
US 2014/0276076 A1   Sep. 18, 2014

Related U.S. Application Data

(60) Provisional application No. 61/787,357, filed on Mar. 15, 2013.

(51) Int. Cl.
*A61B 8/00*   (2006.01)
*A61B 8/08*   (2006.01)
*A61B 8/12*   (2006.01)

(52) U.S. Cl.
CPC .......... *A61B 8/4483* (2013.01); *A61B 8/0891* (2013.01); *A61B 8/12* (2013.01); *A61B 8/445* (2013.01)

(58) Field of Classification Search
CPC ....... A61B 8/00; A61B 8/4483; A61B 8/0891; A61B 8/12; A61B 8/445; A61B 17/22004;

(Continued)

(56) References Cited

U.S. PATENT DOCUMENTS 2,790,095 A   4/1957  Peek et al.
4,014,342 A * 3/1977  Staub ................. A61F 9/00763
                                                606/170

(Continued)

FOREIGN PATENT DOCUMENTS

CN   1188401       7/1998
EP   0 129 878 A2  1/1985

(Continued)

OTHER PUBLICATIONS

International Search Report and Written Opinion issued in PCT/US2013/064570, dated Jan. 24, 2014.

(Continued)

*Primary Examiner* — Carolyn A Pehlke
(74) *Attorney, Agent, or Firm* — Woodard, Emhardt, Henry, Reeves & Wagner, LLP

(57) ABSTRACT

There are disclosed embodiments of devices and methods for imaging the inside of a body part, particularly a blood vessel. In particular embodiments, a catheter has a tip chamber, within which is an ultrasound transducer mounted on a pivot mechanism, a motor for turning the transducer, and an implement for pivoting the transducer. Examples of such an implement are a linear motor, a shaft or filament, and the pivot mechanism may be biased to return to a base position when the implement is not pivoting the transducer. In other embodiments, a mirror reflecting ultrasound signals from the transducer may be rotated and/or pivoted, using similar mechanisms.

18 Claims, 3 Drawing Sheets

(58) Field of Classification Search
CPC ...... A61B 17/8836; A61B 2017/22014; A61C 5/62; A61F 2002/465; A61M 2005/3125; A61M 2205/3306; A61M 2205/50; A61M 5/001; A61M 5/007; A61M 5/31511; A61M 5/445

USPC ............................................................ 600/459

See application file for complete search history.

(56) References Cited

U.S. PATENT DOCUMENTS

| | | | |
|---|---|---|---|
| 4,421,118 A | 12/1983 | Dow et al. | |
| 4,421,508 A * | 12/1983 | Cohen | A61M 5/30 604/70 |
| 4,637,256 A | 1/1987 | Sugiyama et al. | |
| 4,720,266 A | 1/1988 | Leonard et al. | |
| 4,785,816 A | 11/1988 | Dow et al. | |
| 4,811,617 A | 3/1989 | Whitemann, Jr. | |
| 4,834,102 A | 5/1989 | Schwarzchild et al. | |
| 4,930,515 A | 6/1990 | Terwilliger | |
| 4,951,677 A | 8/1990 | Crowley et al. | |
| 4,972,839 A | 11/1990 | Angelsen | |
| 5,168,878 A | 12/1992 | Takano et al. | |
| 5,176,141 A | 1/1993 | Bom et al. | |
| 5,237,884 A | 8/1993 | Seto | |
| 5,240,003 A | 8/1993 | Lancee et al. | |
| 5,373,845 A | 12/1994 | Gardineer et al. | |
| 5,377,682 A | 1/1995 | Ueno et al. | |
| 5,377,685 A | 1/1995 | Kazi et al. | |
| 5,437,283 A * | 8/1995 | Ranalletta | A61B 8/12 600/463 |
| 5,507,294 A | 4/1996 | Lum et al. | |
| 5,535,715 A | 7/1996 | Mouton | |
| 5,611,246 A | 3/1997 | Long et al. | |
| 5,639,097 A * | 6/1997 | Gardner | F16J 15/3452 277/411 |
| 5,729,508 A * | 3/1998 | Baker | H04R 21/028 310/327 |
| 5,770,913 A | 6/1998 | Mizzi | |
| 5,865,751 A | 2/1999 | Yoshiyuki et al. | |
| 5,935,071 A | 8/1999 | Schneider et al. | |
| 6,200,269 B1 | 3/2001 | Lin et al. | |
| 6,241,744 B1 | 6/2001 | Imran et al. | |
| 6,244,600 B1 * | 6/2001 | Leturcq | F16J 15/008 277/353 |
| 6,248,074 B1 | 6/2001 | Ohno et al. | |
| 6,354,814 B1 | 3/2002 | Kaufmann et al. | |
| 6,371,915 B1 | 4/2002 | Koger et al. | |
| 6,599,288 B2 | 7/2003 | Maguire et al. | |
| 6,607,502 B1 | 8/2003 | Maguire et al. | |
| 6,684,094 B1 | 1/2004 | Lehr et al. | |
| 6,689,066 B1 | 2/2004 | Masayoshi et al. | |
| 7,798,971 B2 | 9/2010 | Flesch et al. | |
| 8,206,307 B2 | 6/2012 | Barnard et al. | |
| 8,214,010 B2 | 7/2012 | Courtney et al. | |
| 2002/0016569 A1 * | 2/2002 | Critchlow | A61M 5/14546 604/131 |
| 2002/0062080 A1 | 5/2002 | Okawa et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2003/0073907 A1 | 4/2003 | Taylor | |
| 2005/0203416 A1 | 9/2005 | Angelsen et al. | |
| 2005/0283080 A1 | 12/2005 | Nita et al. | |
| 2006/0030797 A1 | 2/2006 | Zhou et al. | |
| 2006/0173348 A1 | 8/2006 | Wilser et al. | |
| 2006/0253023 A1 | 11/2006 | Lewis et al. | |
| 2007/0038110 A1 | 2/2007 | Flesch et al. | |
| 2007/0038114 A1 | 2/2007 | Couvillon, Jr. | |
| 2007/0062290 A1 | 3/2007 | Roh et al. | |
| 2007/0149917 A1 | 6/2007 | Bennett et al. | |
| 2007/0167813 A1 | 7/2007 | Lee et al. | |
| 2007/0167821 A1 | 7/2007 | Lee et al. | |
| 2007/0239010 A1 | 10/2007 | Johnson | |
| 2008/0097403 A1 | 4/2008 | Donaldson et al. | |
| 2008/0161693 A1 * | 7/2008 | Prager | A61B 8/10 600/459 |
| 2008/0177138 A1 | 7/2008 | Courtney et al. | |
| 2008/0177183 A1 | 7/2008 | Courtney et al. | |
| 2008/0183122 A1 * | 7/2008 | Fisher | A61M 5/31511 604/21 |
| 2008/0221506 A1 | 9/2008 | Rodriguez et al. | |
| 2008/0228081 A1 | 9/2008 | Becker et al. | |
| 2008/0234716 A1 | 9/2008 | Kiester | |
| 2008/0243035 A1 * | 10/2008 | Crunkilton | A61N 7/02 601/2 |
| 2008/0312536 A1 | 12/2008 | Dala-Krishna | |
| 2008/0319376 A1 * | 12/2008 | Wilcox | A61B 17/2202 604/22 |
| 2009/0030312 A1 | 1/2009 | Hadjicostis | |
| 2009/0051121 A1 * | 2/2009 | Solek | F16J 15/3224 277/402 |
| 2009/0088631 A1 | 4/2009 | Dietz et al. | |
| 2009/0306518 A1 | 12/2009 | Kurse et al. | |
| 2010/0036258 A1 | 2/2010 | Dietz et al. | |
| 2010/0145310 A1 * | 6/2010 | Lee | A61B 8/12 604/528 |
| 2010/0160788 A1 | 6/2010 | Davies et al. | |
| 2010/0168577 A1 | 7/2010 | Vezina | |
| 2010/0179426 A1 | 7/2010 | Davies et al. | |
| 2010/0217125 A1 | 8/2010 | Kadokura et al. | |
| 2010/0234689 A1 * | 9/2010 | Wagner | A61B 17/0206 600/210 |
| 2010/0234736 A1 | 9/2010 | Corl | |
| 2010/0249599 A1 | 9/2010 | Hastings et al. | |
| 2010/0249601 A1 | 9/2010 | Courtney | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0021926 A1 | 1/2011 | Spencer et al. | |
| 2011/0071400 A1 | 3/2011 | Hastings et al. | |
| 2011/0071401 A1 | 3/2011 | Hastings et al. | |
| 2011/0166455 A1 | 7/2011 | Cully et al. | |
| 2011/0196286 A1 | 8/2011 | Robertson et al. | |
| 2011/0237955 A1 | 9/2011 | Dietz et al. | |
| 2011/0263986 A1 | 10/2011 | Park et al. | |
| 2011/0301508 A1 | 12/2011 | Sethuraman et al. | |
| 2012/0022379 A1 | 1/2012 | Gubbini et al. | |
| 2012/0108980 A1 | 5/2012 | Shilling et al. | |
| 2012/0172698 A1 | 7/2012 | Teo et al. | |
| 2013/0066304 A1 * | 3/2013 | Belson | A61B 17/00234 606/1 |

FOREIGN PATENT DOCUMENTS

| | | |
|---|---|---|
| EP | 1 977 230 A1 | 10/2008 |
| JP | H03215252 A | 9/1991 |
| JP | H05269133 A | 10/1993 |
| JP | 06-209939 A | 8/1994 |
| JP | 1994-209929 A | 8/1994 |
| JP | 10-262974 A | 10/1998 |
| JP | 1998-262974 A | 10/1998 |
| JP | 2000-126184 A | 5/2000 |
| JP | 2000-15754 A1 | 6/2000 |
| JP | 2001 046367 A | 2/2001 |
| JP | 2001-046375 A | 2/2001 |
| JP | 2002-034981 | 2/2002 |
| JP | 2003 116853 A | 4/2003 |
| JP | 2003 339697 A | 12/2003 |
| JP | 2004/129697 | 4/2004 |
| JP | 2006-325875 A | 12/2006 |
| JP | 2007-267998 A | 10/2007 |
| JP | 2008 075783 A | 4/2008 |
| WO | WO 2012/061643 A1 | 5/2012 |

OTHER PUBLICATIONS

International Search Report and Written Opinion issued in PCT/US2013/064579, dated Jan. 23, 2014.

International Search Report and Written Opinion issued in PCT/US2013/064606, dated Jan. 8, 2014.

(56) References Cited

OTHER PUBLICATIONS

International Search Report and Written Opinion issued in PCT/US2013/064611, dated Jan. 28, 2014.
International Search Report and Written Opinion issued in PCT/US2013/064618, dated Jan. 24, 2014.
International Search Report and Written Opinion issued in PCT/US2013/078245, dated Apr. 25, 2014.
International Search Report and Written Opinion issued in PCT/US2014/023088, dated Aug. 18, 2014, 14 pgs.
International Search Report and Written Opinion issued in PCT/US2014/023092, dated Aug. 12, 2014, 16 pgs.
International Search Report and Written Opinion issued in PCT/US2014/058269, dated Jan. 9, 2015, 17 pgs.
English Abstract of CN 1188401, dated Nov. 16, 2005.
English Abstract of Japanese Publication No. 2008075783.
English Abstract of JP 2000-157547 A, Jan. 25, 2017.
English Abstract of JP 2002-034981 A, dated May 5, 2002.
English Abstract of JP 2006-325875, dated Dec. 7, 2006.
English Abstract of JP H03-215252 A.

\* cited by examiner

INTERNAL ULTRASOUND ASSEMBLY FLUID SEAL

This application claims the benefit of U.S. Provisional Application Ser. No. 61/787,357, filed on Mar. 15, 2013, which is incorporated herein by reference in its entirety.

The present disclosure relates to structure and methods in medical uses of ultrasound. In particular, this disclosure relates to seals around moving parts in medical ultrasound devices.

BACKGROUND

Commonly, devices for subcutaneous medical applications require a motor to couple a moving part in a fluid environment. Fluid environments can present hazardous conditions for certain motors. One example is in the use of ultrasound for imaging, therapy or other medical uses. In such use, ultrasound energy or waves are transmitted through a medium and can reflect, scatter or otherwise attenuate when they reach a surface or border having a significant difference in acoustic impedance. For example, in ultrasound imaging of the human body, ultrasound waves may be applied externally (e.g. by placing a transducer on the skin) or internally (e.g. by placing a transducer within a vessel or organ), and travel through the body's internal fluids, which is a large proportion of water. When the waves strike a bone, organ or other body portion that provides an acoustic interface—i.e., a border of two significantly different acoustic impedances—then the waves are reflected or otherwise attenuated. A transducer (which may be the same transducer that supplied the ultrasound waves or another) receives the reflected or attenuated waves, and an image of a portion of the body can be generated.

A gel is placed between the skin and transducer to reduce reflection or other attenuation between the transducer and the skin. When a transducer is placed within the body, commonly it is inside a protective envelope, such as a tube, catheter or similar housing or enclosure. The material of such an envelope may be selected for its similarity in acoustic impedance to that of bodily fluids, so that there is little or no attenuation as ultrasound waves travel from that material to the fluids or tissues of the body. The inner pocket or volume of the enclosure within which the transducer is placed needs a coupling medium having an acoustic impedance similar to that of the envelope material and the body's fluids, to allow maximum transmission of the ultrasound signal. Without such a medium, e.g. if the inside of the body simply includes air or another gas, significant reflection or other attenuation will occur when the ultrasound energy from the transducer hits the boundary where the gas meets the material of the envelope. Suitable coupling media include biocompatible fluids such as saline, oils such as mineral oil, alcohols, and other fluids.

In ultrasound devices in which the transducer can turn, pivot or otherwise move, a seal between or around mechanisms to move the transducer may be necessary to limit or prevent the coupling medium from corroding, fouling or otherwise interfering with performance of such mechanisms. For example, in mechanisms using a motor that operates a turning or otherwise mobile shaft, with the shaft connected to the transducer or its seat or other holder, a seal may be needed between a chamber holding the transducer and coupling medium and the motor. In another example, a motor is combined with a tool to drill a bore through a clot or plaque in a vein or artery. Corrosive and/or electrolytic coupling media may be incompatible with electrical connections or other parts of a motor, drive shaft or other mechanism. Piezoelectric motors generally need dry conditions to operate, as they require a high friction contact area between a stator and a clutch. If fluid (whether generally corrosive or not) touches that contact area or interface, the friction will be substantially reduced, thereby also reducing the torque output of the motor.

Accordingly, to prevent fluid from contacting parts of such devices, such as motors, a seal should be included between the motor and the fluid environment, to prevent the fluid from gaining access to the motor. Examples of such a structure are disclosed below.

SUMMARY

Among other things, there are shown embodiments of apparatus for ultrasound procedures that include a housing, the housing having a chamber defined at least partially by an acoustic window for transmission of ultrasound signals. The chamber may have a uniform diameter in some embodiments. A transducer for emitting and/or receiving ultrasound signals is within the chamber, and a shaft is operatively connected to the transducer, the shaft adapted to move with respect to the wall in at least one of rotation and translation so that the transducer moves in response to movement of the shaft. A seal partially bounds the chamber, with a part of the seal fixed to the housing and the seal extending across the chamber's diameter, and the seal has an opening through which the shaft extends, with a portion of the seal around the opening engaging the outside of the shaft to create a fluid-tight connection between the seal and the shaft.

As exemplary embodiments, the seal can include a body having a lip portion that is elastically bent with respect to the rest of the body. The lip portion may have a rounded convex surface facing the opening, e.g. with a portion of the rounded convex surface engaging the outside of the shaft to create a fluid-tight connection between the seal and the shaft. A portion of the body can be fixed substantially perpendicular to the housing, and or the lip portion may be substantially annular. If seal has a body including a lip portion, the seal may have a first unstressed position when the shaft does not extend through the opening in which the lip portion is substantially planar with respect to the rest of the body, and a second stressed position when the shaft extends through the opening in which the lip portion is elastically bent with respect to the rest of the body.

The seal may be initially in the shape of a disc with the opening having a diameter smaller than an outer diameter of the shaft. When the shaft extends through the opening, the disc is elastically deformed. In such deformation, the disc can form substantially a portion of a cone in particular examples, and/or be substantially uniformly deformed.

In other embodiments, the seal may include an O-ring and an O-ring holder. For example, such an O-ring holder may engage the shaft with the O-ring fixed to the housing. The shaft is movable with respect to the O-ring holder, and/or the O-ring holder is movable with respect to the O-ring, in some instances. In particular examples the O-ring does not move with the shaft.

Embodiments of apparatus for ultrasound procedures as disclosed below may include a transducer for emitting and/or receiving ultrasound signals, with the transducer being within a chamber that is defined at least partially by a wall forming an acoustic window for transmission of ultrasound signals. The apparatus further includes a motor and a shaft operated by the motor and operatively connected to the transducer. The shaft is adapted to move with respect to the wall in at least one of rotation and translation. A seal is provided next to (e.g. abutting or adjacent) the motor and around at least part of the shaft, the seal engaging the outside of the shaft to create a fluid-tight connection between the seal and the shaft.

Particular examples include a housing that encloses the transducer, the motor, the shaft and the seal. The housing can feature a wall to which the seal is fixed around the entire circumference of the wall. The seal can include an opening smaller than the diameter of the shaft, through which the shaft passes, with at least a portion of the seal bending when the shaft extends through the seal. The seal, in some embodiments, includes a substantially circular line around the opening, wherein when the shaft extends through the seal the seal portion between the line and the opening bends substantially around the line. In other embodiments, seals can include an O-ring and an O-ring holder, the holder having an opening through which the shaft extends, and the O-ring fixed with respect to the wall.

These and other embodiments are discussed further below.

DETAILED DESCRIPTION OF THE ILLUSTRATED EMBODIMENTS

Figure 1:
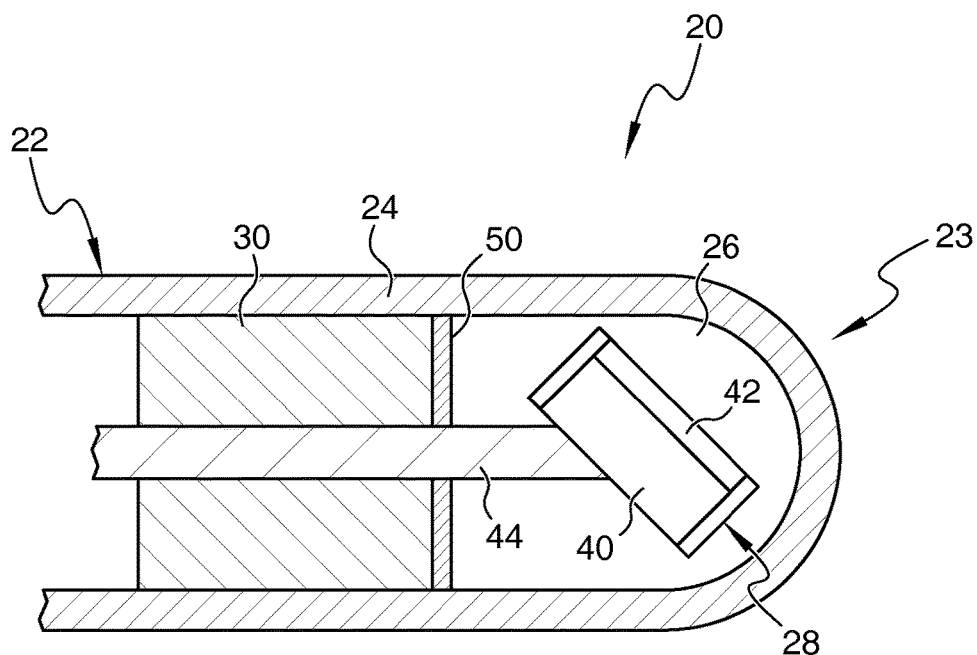
FIG. 1 is a part cross-sectional view of an application end of an embodiment of an ultrasound device as disclosed herein.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there is shown an embodiment of a device 20 for application of ultrasound internally to a patient. Although the embodiment is described herein for use in the context of ultrasound applications, device 20 and the sealing apparatuses described can be used in any number of structural applications in which a motor must be sealed from the fluid environment. As particular examples, device 20 is or is part of a device or system for imaging, such as for intravascular ultrasound (IVUS) imaging. Other embodiments can include devices for therapeutic or diagnostic uses within the body, or for ultrasound devices used outside of the body. In the embodiment indicated schematically in FIG. 1, device 20 is a catheter or other flexible elongated or tubular housing or member 22, and in a particular example is sized and configured for insertion into and/or travel along the vascular system. Member 22 has an application end 23 enclosed by a wall 24, with at least part of wall 24 defining a boundary of internal chamber 26. Wall 24 may be continuous (e.g. monolithic or one-piece), i.e. defining some or all of catheter 22 and encircling or containing chamber 26, or in other embodiments a portion of wall 24 surrounding chamber 26 may be different from and fixed to the rest of catheter 22. Chamber 26 in this embodiment has a uniform diameter, with no steps, corners or sharp irregularities that may undesirably attenuate ultrasound waves. Within catheter 22 and chamber 26 in this embodiment is a transducer 28 for sending and/or receiving ultrasound signals. One or more motors 30 are connected directly or indirectly to transducer 28 so as to turn transducer 28 around a longitudinal axis of device 20, pivot transducer 28 around an axis substantially perpendicular to that longitudinal axis, and/or provide other motions to transducer 28.

Catheter 22 in the illustrated embodiment is an elongated device of plastic or other sturdy flexible material that is substantially transparent to or presenting a minimal barrier to passage of ultrasound signals. For example, when used within a blood vessel containing body tissues and blood, it is preferable for catheter 22 (or at least some or all of wall 24) to be constructed of a material which has acoustic impedances similar to that of body fluids such as blood. Possible materials could include, for example, a polymer material such as high density polyethylene, polymethylpentene (PMP), or acrylonitrile butadiene styrene (ABS). It has been determined that a preferred thickness of at least the portion of catheter 22 which serves as the viewing window should be at least ½ of the wavelength of the center frequency. Alternatively, the thickness can be N*½ of the wavelength, where N is a positive integer.

Wall 24 surrounds chamber 26, which is at the distal end of device 20 in the illustrated embodiment, and extends proximally. Wall 24 is a monolithic part of a catheter 22 in some embodiments, and in others wall 24 is at the application end surrounding all or part of chamber 26. Wall 24 may extend toward the control end of device 20 beyond chamber 26 in some examples. The proximal end of wall 24 and/or catheter 22 may extend outside of the patient during use, and the control end may include a handle or other operating portion (e.g. an imaging system and/or a maneuvering system (not shown)). Particular embodiments of catheter 22 or at least chamber 26 are cylindrical, and are sized for insertion into and passage through blood vessels, such as insertion into the femoral artery and passage through it toward the heart.

Transducer 28 is indicated schematically in the drawings. The term "transducer" should be understood to include an assembly of two or more parts as well as a single piece. For instance, transducer 28 can include a body or backing 40, a transducer element 42 attached to one side of body 40, and a matching layer (not shown) attached to one side of element 42. The matching layer is attached to one side of element 42 and may be focused or non-focused. The matching layer has acoustic impedance generally between that of element 42 and the medium surrounding transducer 28 in order to minimize mismatched acoustic impedance between transducer 28 and the medium surrounding transducer 28 (e.g. mineral oil). In some embodiments, transducer 28 includes an element 42 and matching layer but no body 40. In this embodiment, transducer 28 is pivotable and/or rotatable through action or influence of motor 30, so that with element 42 on the side of body 40 as indicated, a generally lateral (i.e. away from the longitudinal axis) and forward ultrasound beam direction is possible depending on the motion of transducer 28. Body 40 may be substantially opaque to or reflective of ultrasound signals, so that such signals are effectively only projected in one general direction outward from element 42, e.g. to one side or in a limited angular range radially from body 40. Embodiments of transducer 28 may be capable in particular examples of sending and receiving ultrasound waves in a range of frequencies which are typically used in medical ultrasound procedures, such as, for example, in the range from 2 MHz to 50 MHz.

Transducer 28 is electronically connected to a power source and to an imaging system (not shown). Examples of connections include conductors (e.g. wires or cables) along wall 24, through a central lumen of a motor shaft, via slip ring connections, and/or via metallic film(s) along wall 24. Transducer 28 may be mounted in a pivoting mechanism or otherwise linked to motor 30 or a shaft (which rotates, travels longitudinally, or otherwise moves) to permit transducer 28 to turn, pivot, or otherwise move. Embodiments of such examples are discussed and shown in Application Ser. Nos. 61/713,135; 61/713,172; 61/714,275; and 61/748,773, all of which are incorporated by reference in their entireties.

Figure 7:
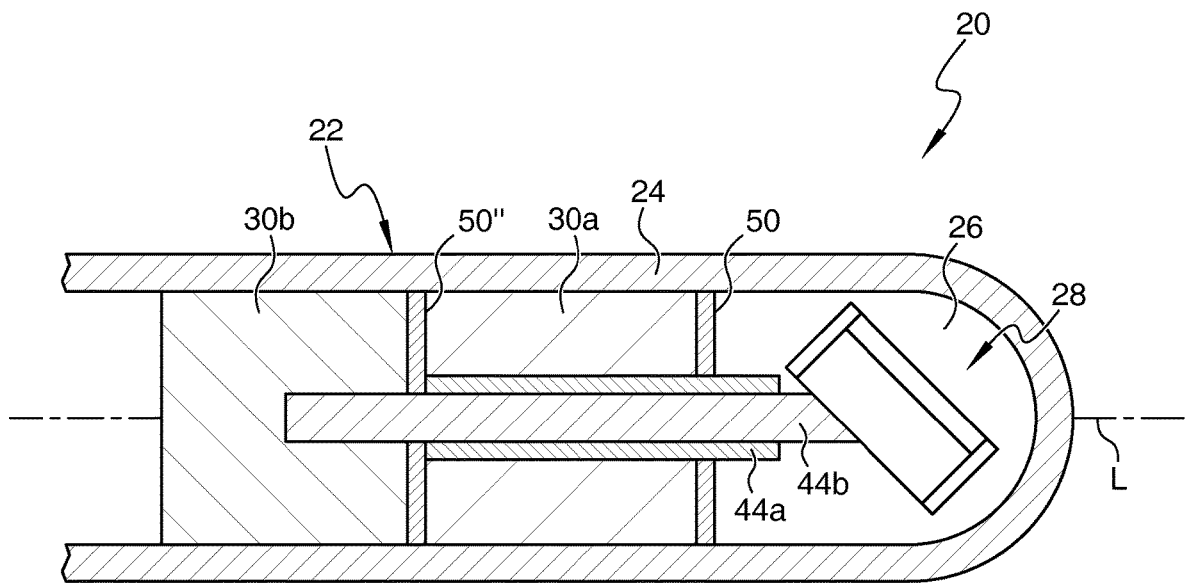
FIG. 7 is a part cross-sectional view of an application end of an embodiment of an ultrasound device as disclosed herein.

Motor 30 may be a rotary or linear motor and includes a shaft 44 for connecting or linking to transducer 28 or a mechanism connected to it. Multiple-motor embodiments are also considered (e.g. FIG. 7), which shows an example of a rotary motor 30a and a linear motor 30b with respective shafts 44a and 44b. In this example, motor 30a turns hollow shaft 44a about a longitudinal axis L of device 20, and shaft 44a is linked to transducer 28 as schematically indicated so that transducer 28 likewise turns around axis L. Motor 30b moves shaft 44b forward and backward along axis L and through shaft 44a in this example, with shaft 44b engaging or linked to transducer 28 off-center. Forward motion of 44b tends to pivot transducer 28 clockwise about an axis into the page (perpendicular to axis L), and rearward motion of shaft 44b tends to pivot or allow pivoting of transducer 28 counterclockwise around an axis into the page.

Embodiments of piezoelectric or electromagnetic micromotors of a size and configuration suitable for containment within catheter 22 may be used. For example, a particular embodiment of a rotary motor (e.g. motor 30a) is a two-phase, coreless, brushless DC electromagnetic motor, which has few components, small size and minimal complexity. A piezoelectric micromotor is of a small size, such as having a diameter in the range from 0.3 mm to 4 mm in particular embodiments, and can exhibit a high torque-to-size ratio. An example of a linear motor (e.g. motor 30b) is an electromagnetic motor similar to a voice coil, used extensively for loudspeakers, which operate by creating a high static magnetic flux (e.g. by a permanent magnet) in the lateral direction (e.g. perpendicular to the longitudinal axis of the motor). An electrically conductive coil is placed through this flux and when current is applied to the coil a force in the axial direction is created, pulling or pushing shaft 44b.

A seal 50 is provided forward of motor 30 (e.g. engaging or adjacent to the forward-most part of motor 30a in the illustrated embodiment) to separate chamber 26 from motor 30. Seal 50 in the illustrated embodiment is a wall or membrane that extends across the entire diameter or width of chamber 26, e.g. contacting wall 24 around a full circumference and forming an end of chamber 26 toward the control end of device 20. Seal 50 may be unitary, formed with or as part of wall 24 and of the same material as wall 24, or may be separately formed and inserted into and joined with the inside of wall 24. For example, seal 50 may be formed concurrently with wall 24, as by molding, or may be separately formed or prepared and fixed to or within wall 24, as by adhesive joining or welding. Outermost portion of seal 50 (e.g. its outer diameter) is attached to wall 24, either in the acoustic window or in the catheter behind it. The attachment may be to an inner surface of wall 24, or to different component such as an end surface of motor 30 so that chamber 26 is isolated from the rest of device 20. In any case, the attachment is to a stationary surface with respect to the movable shaft 44. As indicated in the drawings, one or more shafts (e.g. shafts 44a and/or 44b, associated with motors 30a and/or 30b) extend through seal 50 in order to link or connect to transducer 28. In such embodiments, seal 50 thus provides not only a general wall bounding chamber 26, but also inhibits or prevents flow of fluid out of chamber 26 around shaft(s) 44 extending through seal 50.

Figure 2:
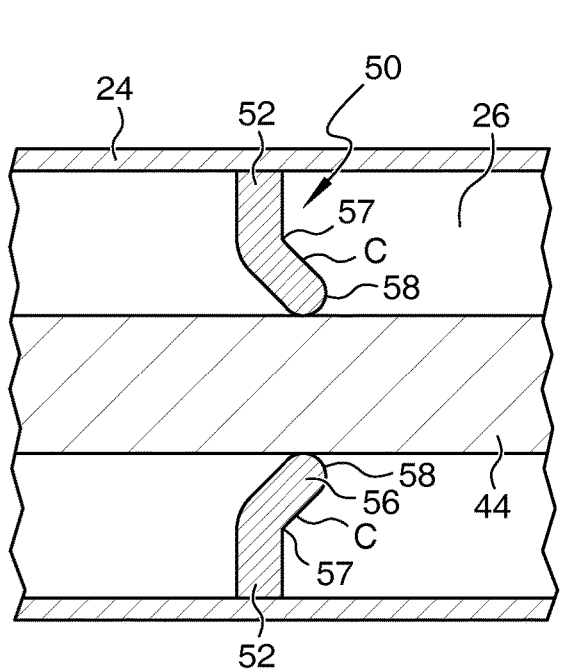
FIG. 2 is a cross-sectional view of an embodiment of a portion of the device of FIG. 1.
Figure 3:
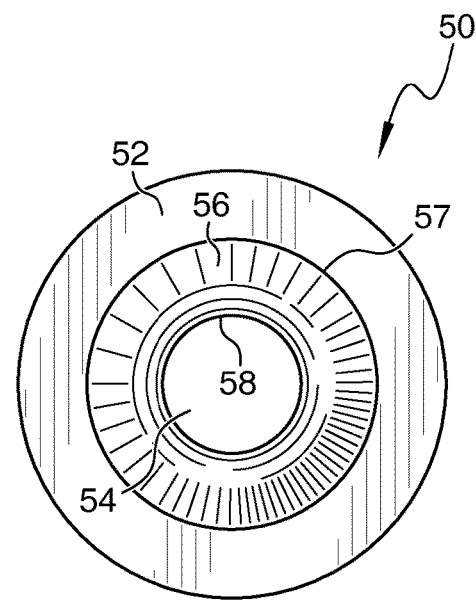
FIG. 3 is an end view of a portion of the embodiment shown in FIG. 2.

A particular embodiment of seal 50 is shown in FIGS. 2-3 which is configured to provide a seal between chamber 26 and motor 30 during rotating motion of shaft 44. Seal 50 is in the form of a disc seal. Seal 50 is a disc of low-friction polymer or elastomer material, and in a particular embodiment of silicone. An opening 54 is in seal 50, and in the illustrated embodiment is in the middle of seal 50 (i.e. along the central longitudinal axis of device 20). Opening 54 is slightly smaller than the outer diameter of shaft 44. Opening 54 is a hole smaller than the diameter of shaft 44 in particular embodiments, and in other embodiments could be a hole combined with a slit, a slit itself, or otherwise configured. In the illustrated embodiment, shaft 44 is centrally located, i.e. along the central longitudinal axis of device 20, and therefore opening 54 is also centrally located. It will be understood that other embodiments may have the location of shaft 44 and opening 54 off-center.

Figure 4:
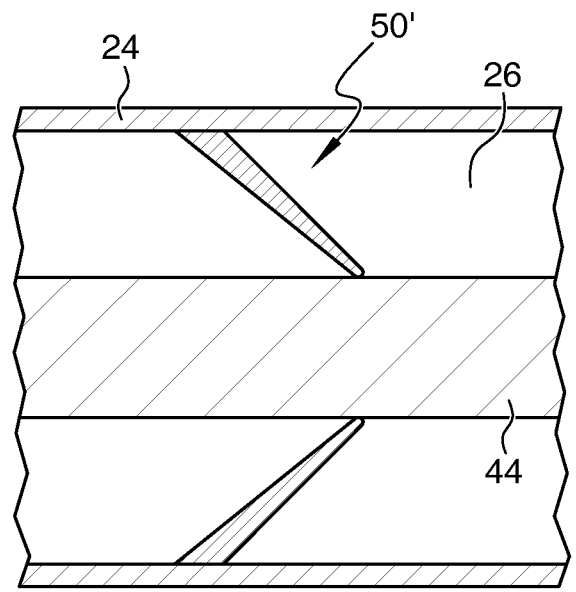
FIG. 4 is a cross-sectional view of an embodiment of a portion of the device of FIG. 1.

As seal 50 is pulled over shaft 44 (or shaft 44 is inserted through seal 50), opening 54 is elastically deformed, enlarging or stretching out over the circumference of shaft 44. The elastic properties of the stretched material of seal 50 causes seal 50 to exert a compressive force or stress on shaft 44 to create a seal between seal 50 and shaft 44. As indicated in the embodiment of FIG. 4, seal 50 may stretch along the length of shaft 44 while remaining attached to wall 24, so that much or all of seal 50 becomes substantially conical and/or reduces in thickness when shaft 44 is forced through it. The low-friction nature of the material of seal 50 permits shaft 44 to turn with minimal hindrance even under some pressure from fluid in chamber 26.

Seal 50 may be formed concurrently with wall 24, or may be separately formed or prepared and fixed to or within wall 24. In other embodiments, seal 50 is attached to other components of device 20 so that chamber 26 is isolated from the rest of device 20, or particularly from motor 30. For example, seal 50 can be attached to an end surface or other portion of the motor 30, or it may be attached to a sheath extending within catheter 22. In any case, the attachment is to a stationary surface with respect to the movable shaft 44. Generally seal 50 is attached to a component which is stationary with respect to wall 24. In any case, the outermost portion of seal 50 (e.g. its outer diameter) is attached either in the acoustic window or in the catheter behind it.

Figure 5:
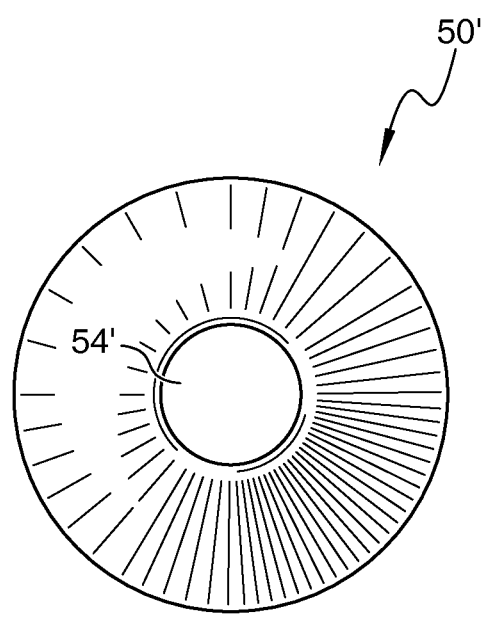
FIG. 5 is an end view of a portion of the embodiment shown in FIG. 4.

A further embodiment is shown in FIGS. 4-5. In that embodiment, seal 50' is configured to provide a seal between chamber 26 and motor 30 during rotation of shaft 44. Seal 50' is a lipped seal made of a low-friction polymer or elastomer. Seal 50' includes a body portion 52, and an opening 54' having a diameter smaller than the shaft 44. Body portion 52 is substantially planar or disc-shaped in this embodiment, extending substantially perpendicular to the longitudinal axis and joining wall 24 so as to form part of the enclosure of chamber 26. The thickness of body portion 52 is preferably uniform, so that the contact between body portion 52 and shaft 44 will be uniform around the circumference of shaft 44.

An annular inner part 56 of body portion 52 surrounds opening 54' and forms a lip. In this embodiment, the lip or annular center 56 is a part that elastically bends as shaft 44 is pressed through it. A line, score or other feature 57 may be placed in body portion 52, for example concentric with opening 54', that promotes bending or provides a particular bending location. An inward surface 58 of annular center 56 that borders or defines opening 54' is rounded in the embodiment illustrated in FIG. 2, to ease insertion of shaft 44 through opening 54' and to ensure that a portion of surface 58 will press evenly and without the potential for gaps on shaft 44 as shaft 44 turns. Surface 58 may describe part of a torus, be convex, and/or describe a semicircle or other part of a curve in cross-section, in specific examples.

In some embodiments, body portion 52 is substantially planar prior to inserting shaft 44 through opening 54'. When device 20 is being assembled, shaft 44 is pressed against body portion 52 at opening 54', and annular part 56 bends away from shaft 44 (e.g. at line or feature 57) to allow shaft 44 to pass through opening 54', without tearing body portion 52. While the part of body portion 52 between annular part 56 and wall 24 of device 20 remains substantially perpendicular to wall 24, as indicated in the embodiment of FIG. 2, annular part 56 angles toward chamber 26 so as to be substantially conical or having a concave surface (e.g. at location C) facing chamber 26. A portion of rounded or convex surface 58 engages shaft 44 around the entire circumference of shaft 44.

Body portion 52 is prepared with annular part 56 already bent to an extent as it is formed or attached in device 20. Insertion of shaft 44 through opening 54' bends annular part 56 at least slightly more (i.e. through elastic deformation) so that surface 58 applies a force to shaft 44 which creates a fluid seal at the engagement of surface 58 and shaft 44. The force effectively seals surface 58 against the outer surface of shaft 44. In some embodiments, fluid pressure from coupling medium in chamber 26 will tend to press annular part 56 against shaft 44, maintaining or strengthening the seal against fluid escaping chamber 26 between annular part 56 of seal 50' and shaft 44.

Figure 6:
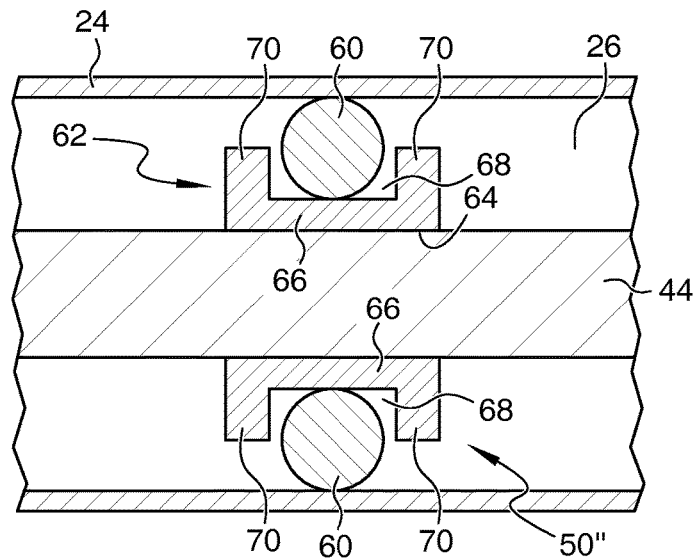
FIG. 6 is a cross-sectional view of an embodiment of a portion of the device of FIG. 1.

FIG. 6 shows an embodiment of seal 50" that is configured for shaft(s) 44 that move longitudinally, including reciprocating longitudinal movement. Seal 50" includes an O-ring 60 and an O-ring holder or gland 62, which together form a fluid-tight barrier between shaft 44 and wall 24. O-ring 60 in the illustrated embodiment is a circular torus of elastomeric or other sealing material, having an outer diameter that engages or abuts against the inner diameter of wall 24.

O-ring holder or gland 62, in the particular illustrated embodiment, is a round, spool-shaped piece having a longitudinal opening 64 for shaft 44 through a body 66. A central groove or space 68 around body 66 is between side flanges 70. The unstressed (i.e. natural) outer diameter of ring 60 is slightly larger than an inner diameter of wall 24, so that when ring 60 is inserted into device 20 a press or interference fit exists between ring 60 and wall 24. The inner diameter of the torus of ring 60 is at least slightly larger than the outer diameter of shaft 44 and at least slightly smaller than the diameter of opening 64. In that way, ring 60 is slightly oversized so that when the ring is placed in space 68 between holder 62 and wall 24, ring 60 is compressed, and the compression force creates a fluid seal between chamber 26 and motor 30.

Holder 62 is of a low-friction material, perhaps similar to the materials noted above with respect to seals 50, 50' to permit easy movement, sliding, or rolling motion of holder 62 with respect to ring 60. In particular embodiments, holder 62 is attached to shaft 44 so that longitudinal movement of shaft 44 moves holder 62 as well. The low-friction material of holder 62 allows ring 60 to move within space 68 (or at least rotate with respect to holder 62). During such movement, the inner diameter of ring 60 engages the diameter of opening 64 as the outer diameter of ring 60 engages the inner diameter of wall 24, preserving the seal. Similarly, ring 60 is able to move longitudinally along wall 24 while preserving the seal. In that way, ring 60 follows holder 62 as holder 62 moves in unison with longitudinal movement of shaft 44. It will be understood that the size of holder 62 and/or the size of space 68 measured along the length of shaft 44 may be related or tailored to the length of travel of shaft 44. That is, the longer space 68 is, the longer ring 60 can move within it and the longer the amount of longitudinal travel of shaft 44 is allowed for, and conversely a shorter distance of travel by shaft 44 may need only a relatively short holder 62 and space 68.

In an alternative embodiment (not shown), holder 62 is shaped in an opposite fashion with respect to axis L. In that embodiment, holder 62 is attached to wall 24 with a space and flanges that are directed inward toward axis L. In that embodiment, the unstressed (i.e. natural) outer diameter of ring 60 is slightly larger than the inner diameter of the space between the flanges of holder 62. The inner diameter of the torus of ring 60 is at least slightly smaller than the outer diameter of shaft 44. In that way, similar to the embodiment of FIG. 6, ring 60 is slightly oversized so that when the ring is placed in the space between holder 62 and shaft 44, ring 60 is compressed, and the compression force creates a fluid seal between chamber 26 and motor 30. In this embodiment ring 60 may move with the longitudinal movement of shaft 44, but holder 62 will remain stationary relative to wall 24 while shaft 44 moves. Ring 60 can move around in holder 62 and still maintain the seal as was explained in the above example.

Specific embodiments of device 20 may have seal(s) 50, 50' and/or 50" having an outer diameter of approximately 2.5 mm, i.e. about the inner diameter of wall 24 and/or chamber 26. An inner diameter of about 0.8 mm for seal(s) 50, 50' and/or 50" is proposed, in light of the expected outer diameter of embodiments of shaft 44. Of course, it will be understood that size and configuration of the outer and inner diameters of seal embodiments may depend on geometry and size of shaft(s) 44, and of wall 24 and/or chamber 26.

It will be understood that features or attributes noted with respect to one or more specific embodiments may be used or incorporated into other embodiments of the structures and methods disclosed. Multiple seals 50, 50' and/or 50" may be used in particular embodiments, as where a first seal is placed at a boundary of chamber 26 and around a first shaft 44a, and a second seal is placed between motor 30a that turns shaft 44a and motor 30b which operates shaft 44b. For example, where shaft 44a is a hollow shaft and shaft 44b operates through the lumen of shaft 44a, a first seal 50 (or other embodiment(s)) is around shaft 44a at the boundary of chamber 26, as discussed above. A second seal 50" (or other embodiment(s)) is between motor 30a and 30b (e.g. attached to or adjacent the rear of motor 30a) and sealingly fitted around shaft 44b. In such a configuration, some liquid from chamber 26 may escape through hollow shaft 44a, i.e. between the inner diameter of shaft 44a and the outer diameter of shaft 44b. Motor 30a in this example can be an electromagnetic motor that is not significantly susceptible to small amounts of escaping coupling medium, which is in any case largely or entirely contained within shaft 44a. The second seal, around shaft 44b and otherwise fixed to catheter 22 (e.g. wall 24), maintains any such escaped coupling medium away from motor 30b.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected.

What is claimed is:

1. An apparatus, comprising:
   a housing, the housing having a uniform-diameter chamber configured for transmission of ultrasound signals, the housing being part of a distal portion of a catheter adapted for use in the vascular system and having a wall;
   a transducer for emitting and/or receiving ultrasound signals, the transducer being within the chamber;
   a motor having a shaft operatively connected to the transducer, the shaft adapted to move with respect to the housing so that the transducer moves in response to movement of the shaft; and
   an O-ring partially bounding the chamber, the O-ring having an opening through which the shaft extends wherein the O-ring moves with the shaft and relative to the wall, wherein a portion of the O-ring engages the shaft or the housing to create a fluid-tight seal.

2. The apparatus of claim 1, further comprising a holder having a space configured to accept the O-ring.

3. The apparatus of claim 2, wherein the holder is attached to the shaft and wherein the O-ring engages the holder and the housing.

4. The apparatus of claim 3, wherein the shaft is adapted to move longitudinally and wherein the O-ring moves with the shaft.

5. The apparatus of claim 2, wherein the holder is attached to the housing and wherein the O-ring engages the holder and the shaft.

6. The apparatus of claim 5, wherein the shaft is adapted to move longitudinally.

7. An apparatus for ultrasound procedures, comprising:
   a housing having a chamber configured for transmission of ultrasound signals, the housing having a wall;
   a transducer for emitting and/or receiving ultrasound signals, the transducer being within the chamber;
   a motor;
   a shaft operated by the motor and operatively connected to the transducer, the shaft adapted to move with respect to the wall in at least one of rotation and translation; and
   an O-ring partially bounding the chamber, and an O-ring holder, the O-ring holder having a body with a longitudinal opening for the shaft and a central space around the body between side flanges, wherein the O-ring holder is between the O-ring and the shaft, and the O-ring is between the wall of the housing and the O-ring holder in the central space of the O-ring holder.

8. The apparatus of claim 1, further comprising a holder having a space configured to accept the O-ring, wherein the holder is attached to the shaft and wherein the O-ring engages the holder and the housing, wherein the shaft is adapted to move longitudinally and wherein the O-ring moves with the shaft.

9. The apparatus of claim 1, further comprising a holder having a space configured to accept the O-ring, wherein the holder is attached to the wall and wherein the O-ring engages the holder and the shaft, wherein the shaft is adapted to move longitudinally and wherein the shaft moves relative to the O-ring.

10. An apparatus, comprising:
    a housing, the housing having a uniform-diameter chamber configured for transmission of ultrasound signals, the housing having a wall;
    a transducer for emitting and/or receiving ultrasound signals, the transducer being within the chamber;
    a shaft operatively connected to the transducer, the shaft adapted to move with respect to the housing so that the transducer moves in response to movement of the shaft;
    an O-ring partially bounding the chamber, the O-ring having an opening through which the shaft extends wherein the O-ring moves with the shaft and relative to the wall, wherein a portion of the O-ring engages the shaft or the housing to create a fluid-tight seal; and an O-ring holder, the O-ring holder having a body with a longitudinal opening for the shaft and a central space around the body between side flanges, wherein the O-ring holder is between the O-ring and the shaft, and the O-ring is between the wall of the housing and the O-ring holder in the central space of the O-ring holder.

11. The apparatus of claim 10, wherein the holder is attached to the shaft and wherein the O-ring engages the holder and the housing.

12. The apparatus of claim 10, wherein the shaft is adapted to move longitudinally and wherein the O-ring moves with the shaft.

13. The apparatus of claim 10, wherein the holder is attached to the housing and wherein the O-ring engages the holder and the shaft.

14. The apparatus of claim 10, wherein the shaft is adapted to move longitudinally.

15. The apparatus of claim 10, further comprising a motor operatively connected to the shaft.

16. The apparatus of claim 15, wherein the motor is a microminiature motor located within the housing.

17. The apparatus of claim 10, wherein the O-ring has an unstressed outer diameter, and the unstressed outer diameter of the O-ring is larger than the uniform diameter of the chamber.

18. The apparatus of claim 10, wherein the O-ring has an unstressed inner diameter and the longitudinal opening of the O-ring holder has an inner diameter, and the unstressed inner diameter of the O-ring is smaller than the inner diameter of the O-ring holder.

* * * * *